(12) United States Patent
Vetter et al.

(10) Patent No.: US 6,817,987 B2
(45) Date of Patent: Nov. 16, 2004

(54) MIXING HYPODERMIC SYRINGE

(75) Inventors: Udo J. Vetter, Ravensburg (DE); Thomas Otto, Weingarten (DE)

(73) Assignee: Arzneimittel GmbH Apotheker Vetter & Co. Ravensburg, Ravensburg (DE)

(*) Notice: Subject to any disclaimer, the term of this patent is extended or adjusted under 35 U.S.C. 154(b) by 0 days.

(21) Appl. No.: 10/222,677

(22) Filed: Aug. 16, 2002

(65) Prior Publication Data

US 2003/0036724 A1 Feb. 20, 2003

(30) Foreign Application Priority Data

Aug. 18, 2001 (DE) .......................................... 101 40 704

(51) Int. Cl.⁷ .............................................. A61M 37/00
(52) U.S. Cl. .......................................... 604/85; 604/92
(58) Field of Search ............................... 604/19, 27, 28, 604/500, 506, 507, 82, 85, 89–92, 145, 181, 182, 187, 191–192, 207–208, 210–211, 218, 220–224

(56) References Cited

U.S. PATENT DOCUMENTS

| | | | | |
|---|---|---|---|---|
| 5,080,649 A | * | 1/1992 | Vetter | ........................ 604/91 |
| 5,139,490 A | * | 8/1992 | Vetter et al. | ................. 604/201 |
| 5,320,603 A | * | 6/1994 | Vetter et al. | ................... 604/82 |
| 5,743,886 A | * | 4/1998 | Lynn et al. | ................. 604/191 |
| 5,833,653 A | * | 11/1998 | Vetter et al. | ................... 604/82 |
| 6,419,656 B1 | * | 7/2002 | Vetter et al. | ................... 604/90 |

\* cited by examiner

Primary Examiner—Brian L. Casler
Assistant Examiner—Michael M. Thompson
(74) Attorney, Agent, or Firm—Herbert Dubno; Andrew Wilford

(57) ABSTRACT

A syringe holding a solvent and a soluble component has a tubular body formed its front and rear ends with a bypass, a plunger axially slidable in the body, and a stem projecting axially rearward out of the body from the plunger. A cover fits over the front end of the body and is so tight that the front compartment can be pressurized to a superatmospheric pressure without leakage out the front end. A free piston slidable in the body forward of the plunger subdivides the body forward of the plunger into a front compartment at the front body end holding the soluble component and a rear compartment between the plunger and the piston and holding the solvent. Stops are provided for arresting the free piston when it is level with the bypass in a position permitting flow through the bypass between the compartments.

14 Claims, 7 Drawing Sheets

MIXING HYPODERMIC SYRINGE

FIELD OF THE INVENTION

The present invention relates to a method of mixing a pair of components, normally a medicament and a solvent. More particularly this invention concerns such a method and a hypodermic syringe for carrying out the method.

BACKGROUND OF THE INVENTION

As described in commonly owned U.S. Pat. No. 6,419,656, a medical syringe has a tubular body extending along an axis and having a front end and a rear end, a plunger axially slidable in the body and carrying a stem projecting axially rearward out of the body from the plunger, and a free piston slidable in the body forward of the plunger and subdividing the body forward of the plunger into a front compartment at the front body end and a rear compartment between the plunger and the piston. The body is formed with a bypass passage forward of the piston in a starting position so the front compartment can hold a soluble medicament and the rear compartment can hold its solvent. Structure at the rear body end forms a radially inwardly open angularly limited cutout and at least two axially spaced, angularly offset, and radially outwardly projecting stop bumps on the stem are axially displaceable through the cutout in respective angularly offset positions of the stem. The stop bumps are axially engageable against the structure except when the stem is in the respective angular position. An elastically deformable brake element engaged between the body and the stem for axially slowing axial forward advance of the stem.

Such a system is extremely effective when the medicament is highly soluble in the solvent. When, however, the medicament is less soluble, it is necessary for the user to shake the syringe in order to ensure proper mixing. Such shaking not only is an annoying step, but also risks damage to the syringe. Furthermore it is inexact at best, so that often the patient is injected before all the medicament is fully dissolved, resulting in clogging of the needle or insufficient dosing.

OBJECTS OF THE INVENTION

It is therefore an object of the present invention to provide an improved method of mixing a medicament and its solvent.

Another object is the provision of an improved mixing syringe which overcomes the above-given disadvantages, that is which allows the user to fully mix even a hard-to-dissolve medicament.

SUMMARY OF THE INVENTION

A syringe holding a solvent and a soluble component has according to the invention a tubular body extending along an axis and having a front end and a rear end and formed therebetween with a bypass, a plunger axially slidable in the body, and a stem projecting axially rearward out of the body from the plunger. A cover fits over the front end of the body and is in accordance with the invention so tight that the front compartment can be pressurized to a superatmospheric pressure without leakage out the front end. A free piston slidable in the body forward of the plunger subdivides the body forward of the plunger into a front compartment at the front body end holding the soluble component and a rear compartment between the plunger and the piston and holding the solvent. Stops are provided for arresting the free piston when it is level with the bypass in a position permitting flow through the bypass between the compartments.

This syringe is used according to the invention by, starting with the plunger and stem in a rearmost end position and the piston at least partially axially rearward of the bypass and separating the solvent from the soluble component, first pressing the plunger and stem axially forward from the rearmost end position into an intermediate position with the plunger rearward of the bypass and thereby pressurizing the rear compartment and forcing the piston forward until the piston in at the bypass and the solvent can flow through the bypass and into the front compartment to mix with the soluble component while gas pressure builds up in the front compartment. When the piston is at the bypass, it is arrested to permit fluid flow in two directions through the bypass past the piston. Then the plunger and stem are released such that gas pressure built up in the front compartment forces the plunger rearward and pumps the solvent and any of the component mixed therewith back through the bypass into the rear compartment.

This pressing and releasing can be done several times to pump the solvent/component mixture back and forth through the bypass between the compartments so as to thoroughly mix them. In this manner even relatively hard-to-dissolve components can be easily and thoroughly dissolved without having to shake the syringe. Normally only a few presses and releases are needed even for the most stubborn substances due to the turbulence of the flow through the bypass which is of restricted flow cross section.

Forward movement of the plunger and stem is stopped in the intermediate position by engagement between formations on the plunger and body. These formations can include short screwthreads on the stem and a short screwthreaded area on the body so that the body must be rotated to advance it forward out of the rearmost position, and then rotated again after mixing is complete to advance it forward from the intermediate position. Instead of screwthreads, bumps can be provided on the stem at angularly and axially offset positions so that the stem has to be twisted to fit the bumps through a notch in the body, such twisting being needed to advance forward from the rear end position and again from the intermediate position.

Once the soluble component in the front compartment is thoroughly mixed with the solvent, according to the invention the front body end is uncovered and fitted with a needle and then the plunger and stem are pushed forward from the intermediate position to press generally all of the solvent/component mixture in the rear compartment into the front compartment until the plunger rearwardly engages the piston. Further forward advance of the plunger, stem, and piston expresses the solvent/component mixture out the front end of the syringe body.

BRIEF DESCRIPTION OF THE DRAWING

The above and other objects, features, and advantages will become more readily apparent from the following description, reference being made to the accompanying drawing in which:

FIG. 7A is a section taken along line VIIA—VIIA of FIG. 7;

Figure 7:
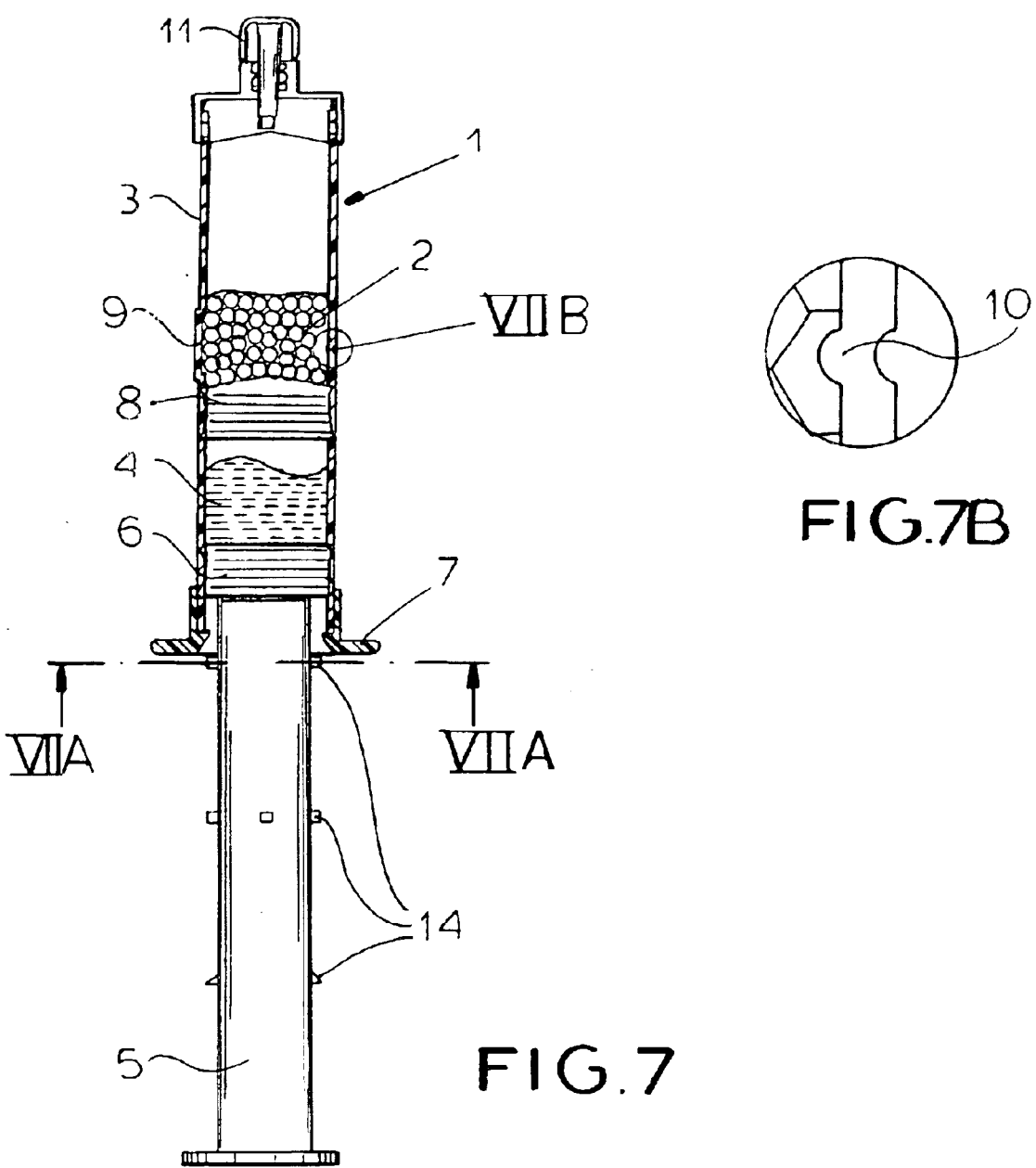
FIG. 7 is a view like FIG. 1 of another syringe in accordance with the invention.
Figure 8:
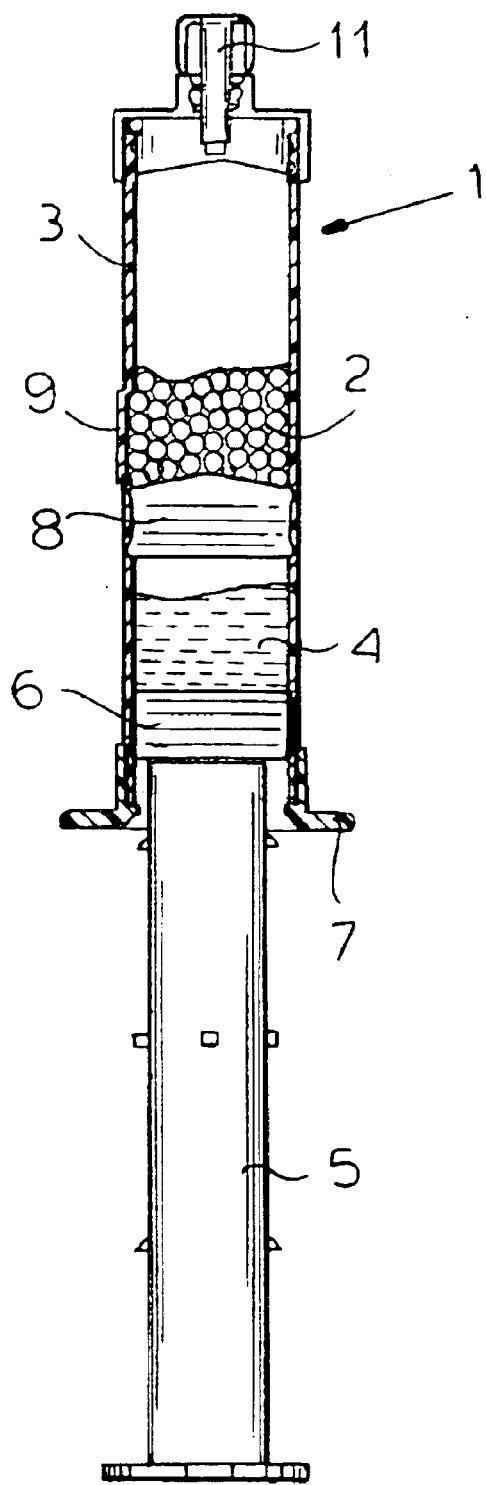
Figure 9:
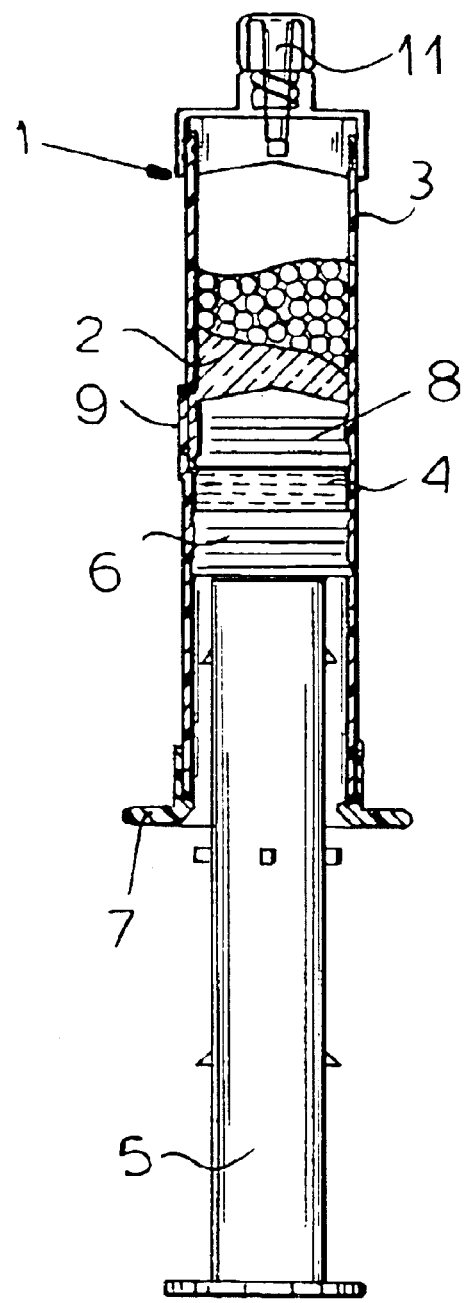
Figure 10:
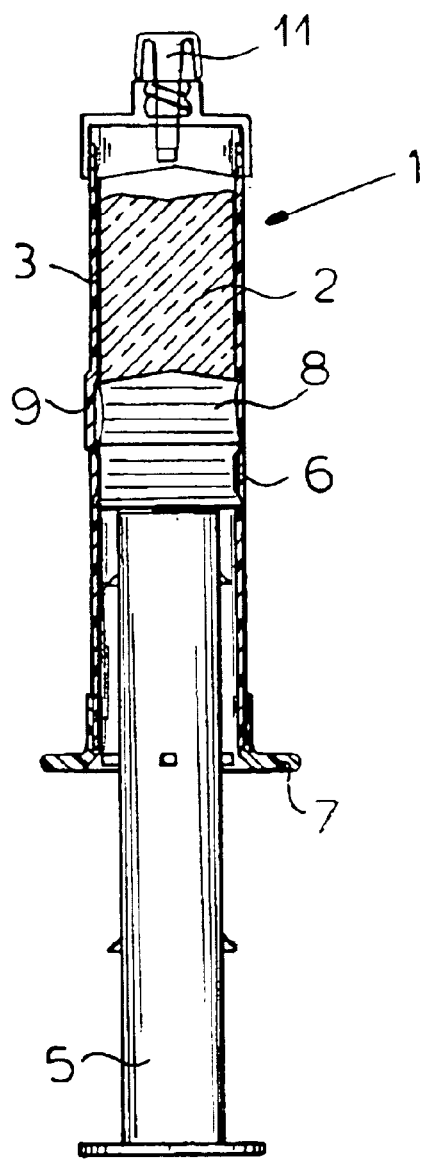
Figure 11:
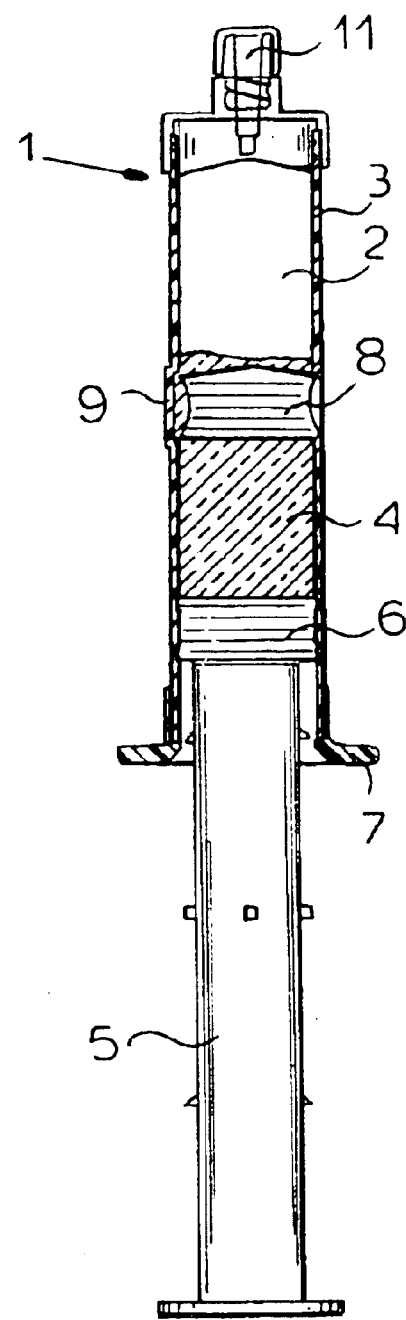
Figure 12:
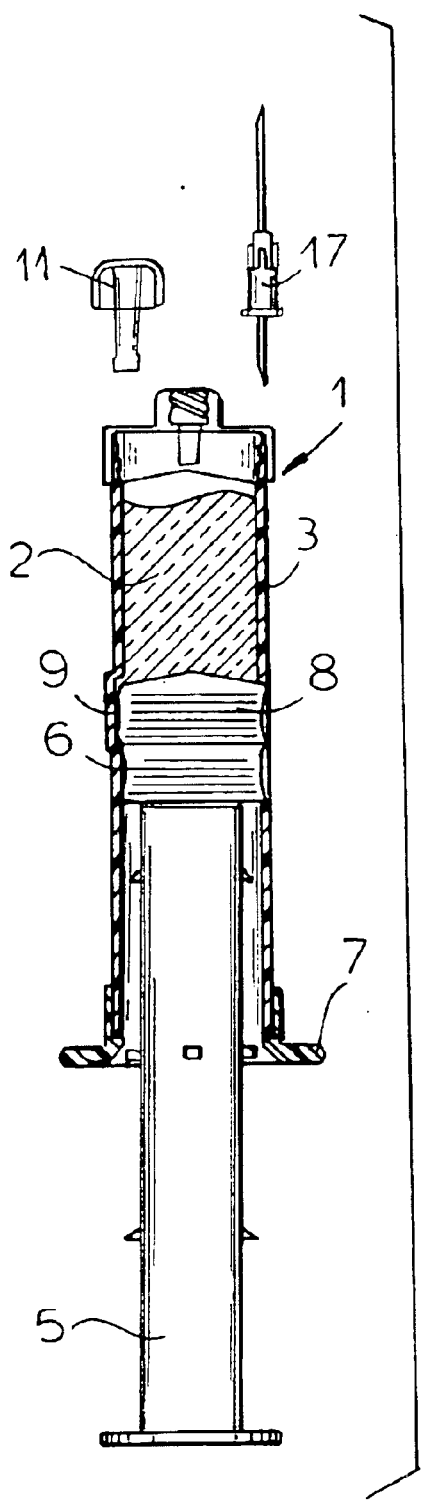

FIG, 7B is a large-scale view of the detail indicated at VIIB in FIG. 7; and

FIGS. 8 through 13 are views like FIG. 7 showing use of the FIG. 7 syringe.

SPECIFIC DESCRIPTION

Figure 1:
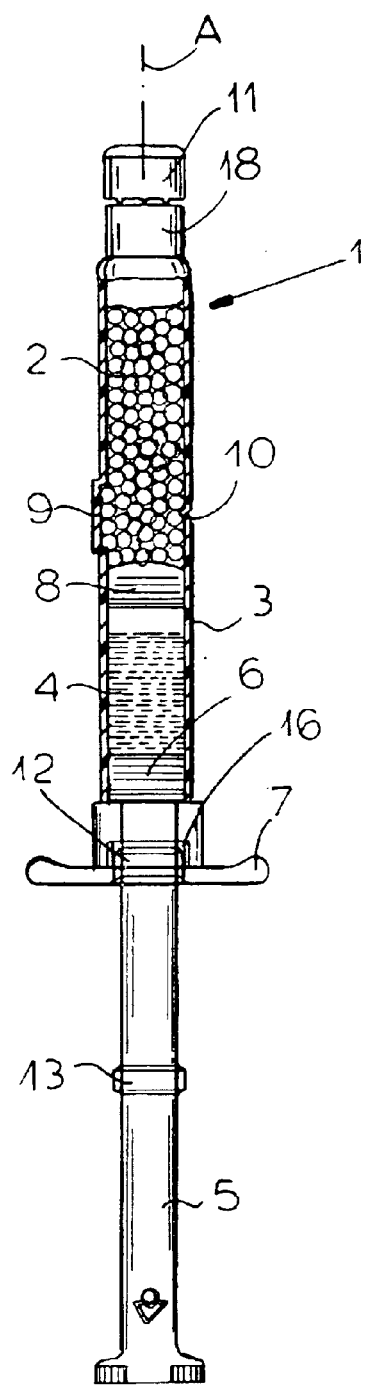
FIG. 1 is an axial section through a syringe for carrying out the method of this invention.
Figure 6:
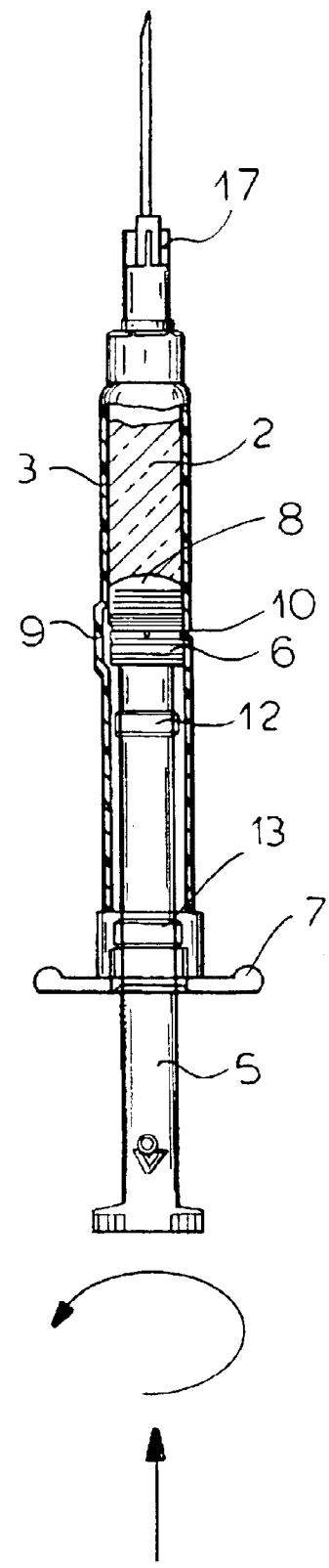

As seen in FIG. 1, a syringe 1 has a basically tubular glass or plastic body 3 centered on an axis A and slidably receiving a plunger 6. A rod or stem 5 projects axially rearward from the plunger 6 through a finger-brace end cap 7. A free piston 8 subdivides the tubular body 3 forward of the plunger 6 into a front compartment 2 that is to start with filled with gas and a soluble medicament, normally in lyophilized powder form, and a rear compartment 4 that to start with is filled with a liquid solvent for the medicament. A radially inwardly open and axially extending bypass groove 9 is formed in the tubular body 3 forward of the piston 8 in the FIG. 7 starting position. Initially the front end of the tubular body 3 is covered by a cap 11 which is replaced for use by a needle or cannula 17 (FIG. 6). The rear end of the tubular body 3 is formed with a short internal screwthread 16 and the stem 5 is formed with a complementary front external screwthread 12 and a similar rear external screwthread 13.

Figure 2:
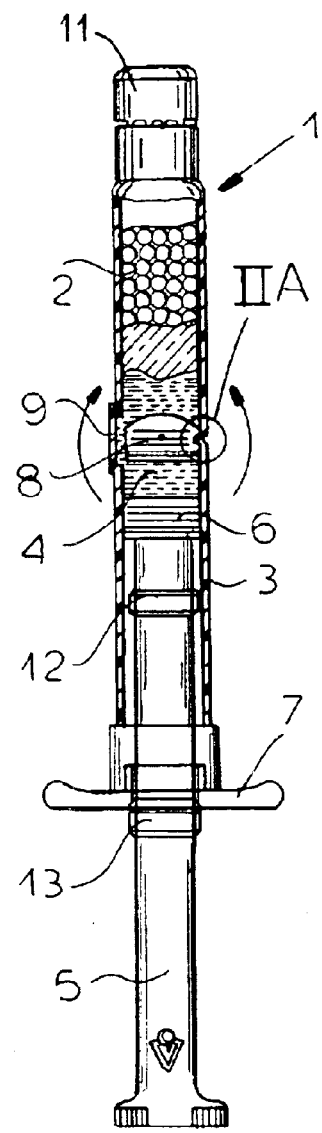
FIG. 2 is a view like FIG. 1 at the start of a mixing operation.
Figure 2A:
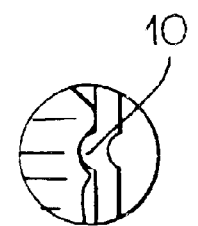
FIG. 2A in a large-scale view of the detail indicated at IIA in FIG. 2.

According to the invention the syringe body 3 is formed with an internal stop bump 10 shown in FIG. 2A and adapted to fit in a complementary outwardly open recess or groove of the piston 8 when same is in a position sitting generally centrally in the bypass 9. In addition the piston 8 has an axial length substantially shorter than the bypass 9 so that, when arrested by the stop 10, fluid can flow axially past it through the bypass 9, which can be formed by several axially extending and radially inwardly open grooves. Also according to the invention the cap 11 is constructed such that it can withstand considerable pressure, allowing the front compartment 2 to be pressurized at a significant superatmospheric pressure. This is typically achieved by making it a two-part structure, with a holding ring 18 that must be broken and removed before the cap 11, which secures in place an unillustrated elastomeric plug, can be stripped off.

In accordance with the invention the syringe 1 starts in the position shown in FIG. 1. The front screwthread 12 of the stem 5 is threaded with the rear-end body screwthread 16 and the plunger or rear plunger 6 is retracted to the extreme rear end of the body 3. The front piston 8 is positioned axially somewhat rearward of the bypass 9 no that the lyophilized dry medicament in the front compartment 2 is completely separated from the aqueous solvent in the rear compartment.

To start with the stem 5 is rotated to move the screwthread 12 axially forward through the screwthread 16 and then the plunger 6 and stem 5 are advanced as shown in FIG. 2. The relatively incompressible solvent in the rear compartment 4 pushes the piston 8 forward until it is in the middle of the bypass 9 and the stop bump 10 arrests it, whereupon the solvent flows through the bypass into the front compartment 2. This action compresses the sterile gas in the front compartment 2 and mixes the solvent with the medicament as shown by the dashed-line/solid-line hatching. Forward movement of the piston 8 and stem 5 is stopped when the rear stem screwthread 13 axially abuts the body screwthread 16.

Figure 3:
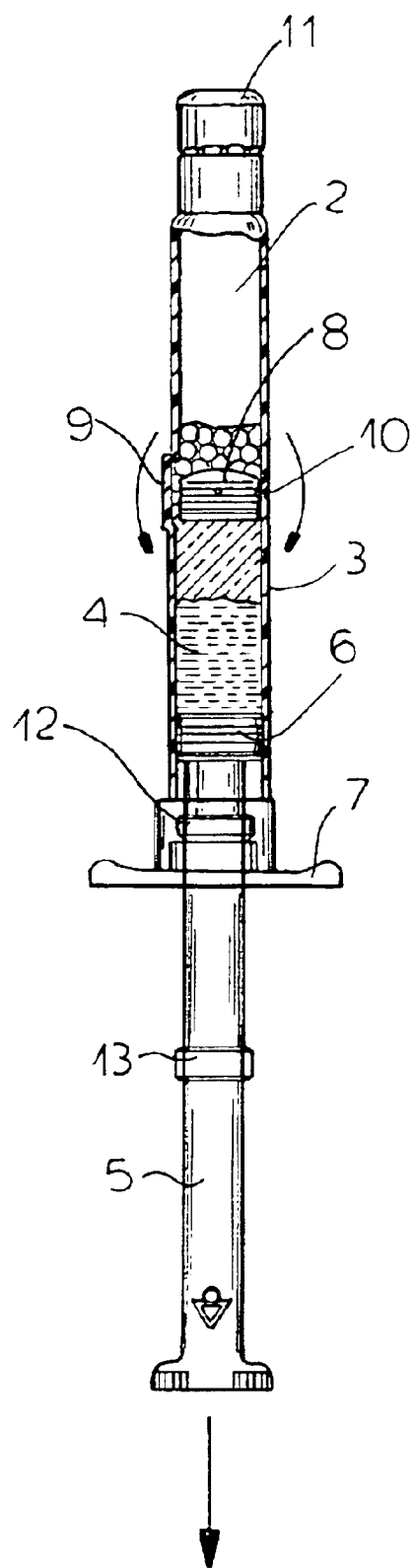
FIGS. 3, 4, 5, and 6 are views like FIG. 1 illustrating further steps in the operation of the syringe of FIG. 1.
Figure 4:
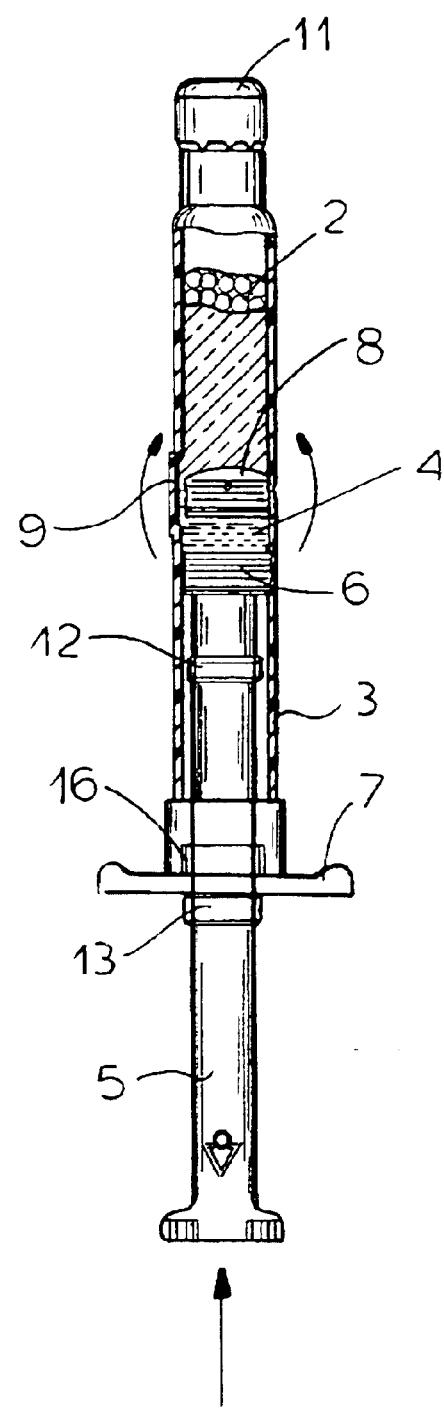
Figure 5:
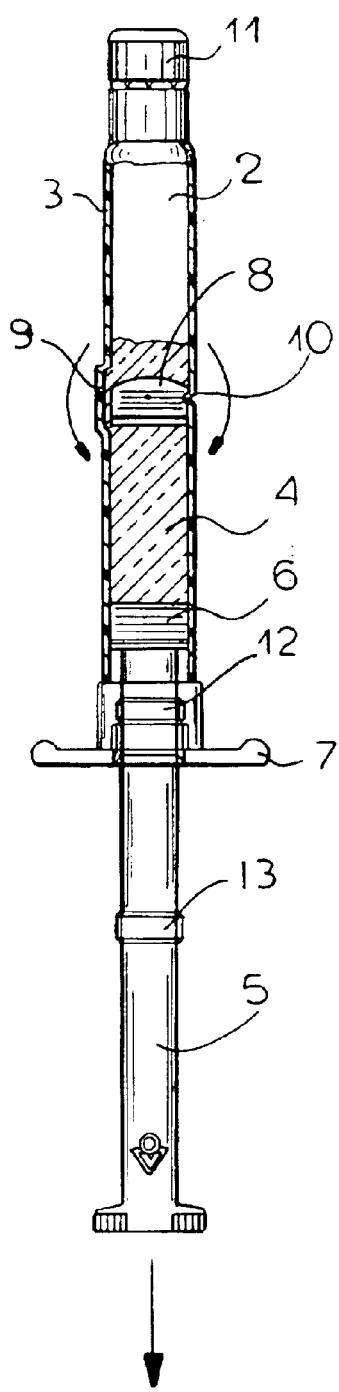

The user then releases the stem 5 so that the pressure in the front compartment 2 forces the contents of this compartment 2 back through the bypass into the rear compartment 4 as indicated in FIG. 3, further mixing the solvent and the medicament. The user then advances the stem 5 again as shown in FIG. 4 to pump the mixture (still shown in dashed-line/solid-line hatching) forward into the front compartment 2 and dissolve even more of the medicament. This process is repeated until as shown in FIG. 5 all of the medicament is dissolved. Forcing the solvent back and forth through the constriction constituted by the bypass 9 very effectively mixes the solvent and medicament, so that normally only a few presses on the stem 5 are needed to thoroughly mix them.

Finally the cap 11 is removed and replaced with a standard Luer-type needle or cannula 17 as shown in FIG. 6 while the stem 5 and plunger 6 are in their rear end positions so that the compartment is generally depressurized or at atmospheric pressure. The stem 5 is then rotated to move the screwthread 13 forward through the screwthread 16, whereupon the plunger 6 can be pressed against the rear end of the piston 8 to express the mixture from the cannula 17. The total axial length of the pistons 6 and 8 is greater than that of the bypass 9 so that this can be done with no significant loss or leakage backward of the mixture. Once emptied, the unit is discarded.

Figure 13:
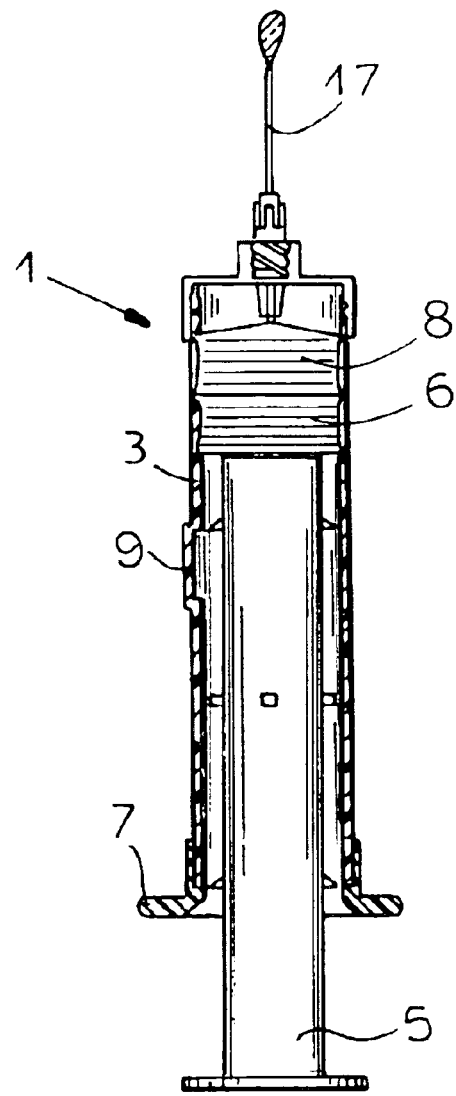

In FIGS. 7 through 18 an arrangement is shown which has, instead of the screwthread 12, 13, and 16, three axially spaced sets of radially projecting bumps 14 on the stem 5 and inwardly projecting ribs defining complementary radially inwardly open notches 15 in the rear body end. Thus starting from the position of FIGS. 7 and 8 the stem 5 has to be rotated to fit the frontmost set of bumps 14 through the notches 15 to allow pumping and mixing in the position of PIGS. 9 through 12 with the middle set of bumps 14 limiting forward advance of the stem 5. Then the stem 5 is rotated again after mixing of the syringe contents as shown in FIG. 13 to allow the middle set of bumps 14 to pass through the notches 15 and allow expressing of the mixed contents. Once the syringe is emptied, the stem 5 is twisted again to lock the rearmost set of bumps 14 forward of the notches 15.

What is claimed is:

1. A syringe comprising:

a tubular body extending along an axis and having a front end and a rear end and formed therebetween with a bypass;

a plunger axially slidable in the body;

a stem projecting axially rearward out of the body from the plunger a cover over the front end of the body and sufficiently tight to allow superatmospheric pressurization of the front compartment;

a free piston slidable in the body forward of the plunger and subdividing the body forward of the plunger into a front compartment at the front body end holding the soluble medicament and a rear compartment between the plunger and the piston and holding the solvent, whereby when the plunger and stem are pressed axially forward from a rearmost end position into an intermediate position to pressurize the rear compartment and force the piston forward until the piston is at the bypass and the solvent can flow through the bypass into the front compartment to mix with the soluble medicament with build up of gas pressure in the front compartment; and stop means for arresting the piston when it is at the bypass for permitting fluid flow in two directions through the bypass past the piston while still permitting free axial movement of the plunger, whereby gas pressure in the front compartment can force the plunger rearward and pump the solvent and any of the medicament mixed therewith back past the arrested piston and through the bypass into the rear compartment.

2. The syringe defined in claim 1 wherein the stop means is interengageable radially extending formations on the body and piston.

3. The syringe defined in claim 2 wherein the formations include a radially inwardly projecting bump on the body and a complementary radially outwardly open recess on the piston.

4. The syringe defined in claim 1, further comprising
means including stops on the stem and body for inhibiting forward movement of the plunger past the intermediate position.

5. The syringe defined in claim 4 wherein the stops include screwthread formations on the stem and body, whereby the stem has to be rotated about the axis for movement forward past the intermediate position.

6. The syringe defined in claim 5 wherein the screwthread on the stem is of limited axial extent.

7. The syringe defined in claim 4 wherein the stops include screwthread formations on the stem and body, whereby the stem has to be rotated about the axis for movement forward past the rear end position.

8. The syringe defined in claim 7 wherein the screwthread on the stem is of limited axial extent.

9. The syringe defined in claim 4 wherein the stops include at least one radially projecting bump on the stem and at least one radially inwardly open notch through which the bump can pass axially on the body, whereby the stem has to be rotated about the axis and angularly position for movement forward past the intermediate position.

10. The syringe defined in claim 4 wherein the stops include at least one radially projecting bump on the stem and at least one radially inwardly open notch through which the bump can pass axially on the body, whereby the stem has to be rotated about the axis and angularly position for movement forward past the rear end position.

11. A method of operating a syringe having:
a tubular body extending along an axis and having a front end and a rear end and formed therebetween with a bypass,
a plunger axially slidable in the body;
a stem projecting axially rearward out of the body from the plunger
a cover over the front end of the body; and
a free piston slidable in the body forward of the plunger and subdividing the body forward of the plunger into a front compartment at the front body end and a rear compartment between the plunger and the piston the method comprising the steps, after having provided the front compartment with a charge of compressible gas and a dose of a dry soluble medicament and the rear compartment with a liquid solvent for the medicament and starting with the plunger and stem in a rearmost end position and the piston at least partially axially rearward of the bypass and separating the solvent from the soluble medicament, of:

a) pressing the plunger and stem axially forward from the rearmost end position into an intermediate position with the plunger rearward of the bypass and thereby pressurizing the rear compartment and forcing the piston forward until the piston is at the bypass and the solvent can flow through the bypass and into the front compartment to mix with the soluble medicament while maintaining the front end closed such that gas pressure builds up in the front compartment;

b) when the piston is at the bypass, arresting the piston at the bypass and permitting fluid flow in two directions through the bypass past the piston; and c) releasing the plunger and stem such that gas pressure built up in the front compartment forces the plunger rearward and pumps the solvent and any of the medicament mixed there-with back past the arrested piston and through the bypass into the rear compartment.

12. The syringe-operating method defined in claim 11, further comprising:
stopping forward movement of the plunger and stem in the intermediate position by engagement between formations on the plunger and body.

13. The syringe-operating method defined in claim 11, further comprising the step of
d) repeating steps a) and c) while continuing to arrest the piston at the bypass to pump the solvent back and forth between the compartments and thereby thoroughly mix the solvent and medicament.

14. The syringe-operating method defined in claim 11, further comprising the steps after step c) of sequentially:
e) uncovering the front body end;
f) pushing the plunger and stem forward from the intermediate position and thereby pressing generally all of the solvent/medicament mixture in the rear compartment into the front compartment until the plunger rearwardly engages the piston; and
g) pushing the plunger, stem, and piston forward to express the solvent/medicament mixture out the front end of the syringe body.

* * * * *